(12) United States Patent
Rozental

(10) Patent No.: US 9,770,360 B2
(45) Date of Patent: Sep. 26, 2017

(54) THERAPEUTIC BRAIN COOLING SYSTEM AND SPINAL CORD COOLING SYSTEM

(76) Inventor: Renato Rozental, Hartsdale, NY (US)

( * ) Notice: Subject to any disclaimer, the term of this patent is extended or adjusted under 35 U.S.C. 154(b) by 516 days.

(21) Appl. No.: 13/806,381

(22) PCT Filed: Jun. 29, 2011

(86) PCT No.: PCT/US2011/042440
§ 371 (c)(1),
(2), (4) Date: Jan. 14, 2013

(87) PCT Pub. No.: WO2012/006184
PCT Pub. Date: Jan. 12, 2012

(65) Prior Publication Data
US 2013/0211484 A1    Aug. 15, 2013

Related U.S. Application Data

(60) Provisional application No. 61/359,476, filed on Jun. 29, 2010.

(51) Int. Cl.
*A61F 7/00*    (2006.01)
*A42B 3/10*    (2006.01)
(Continued)

(52) U.S. Cl.
CPC .............. *A61F 7/10* (2013.01); *A42B 3/122* (2013.01); *A42B 3/285* (2013.01); *A61F 7/02* (2013.01);
(Continued)

(58) Field of Classification Search
CPC ...... A61F 2007/0002; A61F 2007/0008; A61F 2007/0091; A61F 2007/0092; A61F 2007/0233; A42B 1/008; A42B 3/122
(Continued)

(56) References Cited

U.S. PATENT DOCUMENTS 1,627,523 A * 5/1927 Morris .......................... 607/109
4,035,846 A * 7/1977 Jencks ................... A42B 3/122
2/413

(Continued)

FOREIGN PATENT DOCUMENTS

WO    01/39692 A2    6/2001

OTHER PUBLICATIONS

Wouter Stomp, Non-Invasively Measuring Brain Temperature, MedGadget.com (May 31, 2011) available at http://medgadget.com/2011/05/noninvasively_measuring_brain_temperature-2.html (last visited Jun. 20, 2011).
(Continued)

*Primary Examiner* — Kaitlyn Smith
(74) *Attorney, Agent, or Firm* — Ascenda Law Group, PC

(57) ABSTRACT

This disclosure relates to a brain cooling and spinal cord cooling system, device or mechanism for use in military helmets, and in an adapted format in non-military helmets. The system is comprised of an inflatable pad, or a set of interconnected pads, attached to the interior surface of the helmet, together with a series of valves that allow cooling gases to be delivered from a high pressure canister. The use of different cooling gases permits the achievement and maintenance of cooling of the brain for 24 to 96 hours at a mild (36° C.) or moderate (33° C.-35° C.) brain hypothermia, which is 1.5° C.-4.5° C. below the core temperature.

25 Claims, 8 Drawing Sheets

(51) Int. Cl.
  *A61F 7/10* (2006.01)
  *A42B 3/12* (2006.01)
  *A42B 3/28* (2006.01)
  *A61F 7/02* (2006.01)

(52) U.S. Cl.
  CPC ............ *A61F 2007/0008* (2013.01); *A61F 2007/0024* (2013.01); *A61F 2007/0086* (2013.01); *A61F 2007/0092* (2013.01); *A61F 2007/0095* (2013.01); *A61F 2007/0228* (2013.01); *A61F 2007/0233* (2013.01)

(58) Field of Classification Search
  USPC .................................................. 607/109, 110
  See application file for complete search history.

(56) References Cited

U.S. PATENT DOCUMENTS

| | | | |
|---|---|---|---|
| 4,147,921 A * | 4/1979 | Walter et al. | 219/211 |
| 4,172,495 A * | 10/1979 | Zebuhr et al. | 165/46 |
| 4,552,149 A | 11/1985 | Tatsuki | |
| 4,586,200 A * | 5/1986 | Poon | A42B 3/122 2/413 |
| 4,691,762 A | 9/1987 | Elkins et al. | |
| 4,753,242 A | 6/1988 | Saggers | |
| 5,050,240 A * | 9/1991 | Sayre | A42B 3/122 137/38 |
| 5,090,054 A * | 2/1992 | Grilliot et al. | 2/5 |
| 5,259,071 A * | 11/1993 | Scott | A42B 3/122 2/410 |
| 5,261,399 A | 11/1993 | Klatz et al. | |
| 5,263,203 A * | 11/1993 | Kraemer | A42B 3/122 2/413 |
| 5,365,607 A * | 11/1994 | Benevento et al. | 2/181.4 |
| 5,539,934 A | 7/1996 | Ponder | |
| 5,603,728 A * | 2/1997 | Pachys | 607/110 |
| 5,871,526 A * | 2/1999 | Gibbs | A61F 7/02 165/46 |
| 5,913,885 A | 6/1999 | Klatz et al. | |
| 5,957,964 A | 9/1999 | Ceravolo | |
| 6,030,412 A | 2/2000 | Klatz et al. | |
| 6,126,680 A | 10/2000 | Wass | |
| 6,126,683 A * | 10/2000 | Momtaheni | 607/109 |
| 6,178,560 B1 * | 1/2001 | Halstead | A42B 3/122 2/413 |
| 6,178,562 B1 * | 1/2001 | Elkins | 2/458 |
| 6,183,501 B1 | 2/2001 | Latham | |
| 6,277,143 B1 * | 8/2001 | Klatz et al. | 607/104 |
| 6,312,453 B1 | 11/2001 | Stefanile et al. | |
| 6,351,853 B1 * | 3/2002 | Halstead | A42B 3/122 2/413 |
| 6,416,532 B1 | 7/2002 | Fallik | |
| 6,461,379 B1 | 10/2002 | Carson et al. | |
| 6,591,428 B2 * | 7/2003 | Halstead | A42B 3/122 2/413 |
| 6,682,552 B2 | 1/2004 | Ramsden et al. | |
| 6,962,600 B2 | 11/2005 | Lennox et al. | |
| 6,969,399 B2 | 11/2005 | Schock et al. | |
| 6,986,783 B2 | 1/2006 | Gunn et al. | |
| 7,008,445 B2 | 3/2006 | Lennox | |
| 7,052,509 B2 | 5/2006 | Lennox et al. | |
| 7,056,282 B2 | 6/2006 | Chester et al. | |
| 7,056,334 B2 | 6/2006 | Lennox | |
| 7,077,858 B2 | 7/2006 | Fletcher et al. | |
| 7,087,075 B2 | 8/2006 | Briscoe et al. | |
| 7,179,279 B2 | 2/2007 | Radons et al. | |
| 7,303,579 B2 | 12/2007 | Schock et al. | |
| 7,507,250 B2 | 3/2009 | Lennox | |
| 7,565,705 B2 | 7/2009 | Elkins et al. | |
| 7,621,945 B2 | 11/2009 | Lennox et al. | |
| 7,637,931 B2 * | 12/2009 | Heaton | 607/104 |
| 7,744,640 B1 * | 6/2010 | Faries et al. | 607/109 |
| 7,846,118 B2 | 12/2010 | Sandhu | |
| 8,226,698 B2 * | 7/2012 | Edelman et al. | 607/104 |
| 8,262,601 B2 * | 9/2012 | Cumming et al. | 602/74 |
| 8,529,613 B2 * | 9/2013 | Radziunas et al. | 607/110 |
| 2002/0058976 A1 * | 5/2002 | Lee | 607/110 |
| 2002/0100106 A1 * | 8/2002 | Simmons | 2/171.2 |
| 2002/0138033 A1 * | 9/2002 | Elkins | 604/6.13 |
| 2002/0152541 A1 * | 10/2002 | Halstead | A42B 3/122 2/413 |
| 2003/0060863 A1 * | 3/2003 | Dobak, III | 607/104 |
| 2003/0088299 A1 * | 5/2003 | Magers et al. | 607/104 |
| 2003/0105435 A1 * | 6/2003 | Taylor | 604/252 |
| 2003/0130651 A1 * | 7/2003 | Lennox | 606/21 |
| 2004/0064171 A1 | 4/2004 | Briscoe et al. | |
| 2004/0107482 A1 * | 6/2004 | Picotte | A42B 1/08 2/411 |
| 2004/0158303 A1 * | 8/2004 | Lennox et al. | 607/109 |
| 2004/0226077 A1 * | 11/2004 | Toth | 2/411 |
| 2005/0107855 A1 * | 5/2005 | Lennox et al. | 607/104 |
| 2005/0177212 A1 * | 8/2005 | Njemanze | 607/104 |
| 2005/0255307 A1 * | 11/2005 | Dennis et al. | 428/304.4 |
| 2005/0268383 A1 * | 12/2005 | Harris | 2/413 |
| 2006/0004426 A1 * | 1/2006 | Heaton | 607/104 |
| 2006/0030915 A1 | 2/2006 | Lennox et al. | |
| 2006/0030916 A1 * | 2/2006 | Lennox | 607/104 |
| 2006/0122673 A1 * | 6/2006 | Callister et al. | 607/105 |
| 2006/0161200 A1 * | 7/2006 | Fallah | A61H 1/0292 606/204.15 |
| 2006/0293734 A1 * | 12/2006 | Scott et al. | 607/105 |
| 2007/0000025 A1 * | 1/2007 | Picotte | A42B 1/08 2/171 |
| 2007/0112401 A1 * | 5/2007 | Balachandran et al. | 607/104 |
| 2008/0021335 A1 * | 1/2008 | Harada | 600/504 |
| 2008/0244801 A1 * | 10/2008 | Russo | 2/22 |
| 2008/0269852 A1 * | 10/2008 | Lennox | A61F 7/02 607/104 |
| 2010/0137951 A1 * | 6/2010 | Lennox et al. | 607/104 |
| 2010/0161013 A1 | 6/2010 | Heaton | |
| 2010/0186436 A1 * | 7/2010 | Stormby | 62/259.3 |
| 2010/0211140 A1 | 8/2010 | Barbut et al. | |
| 2011/0094012 A1 * | 4/2011 | Toth | 2/171.2 |
| 2012/0130457 A1 * | 5/2012 | Gammons et al. | 607/104 |
| 2012/0310312 A1 * | 12/2012 | Yee | 607/105 |
| 2016/0166428 A1 * | 6/2016 | Hilton | A61F 7/02 607/104 |

OTHER PUBLICATIONS

Mellegard et al., A method for monitoring intracerebral temperature in neurosurgical patients, Neurosurgery, 27, 654-57 (1990).
Hayward et al., Role of cerebral arterial blood in the regulation of brain temperature in the monkey, Am J Physiol, 215, 389-403 (1968).
Whitby et al., Cerebral, Esophageal and nasopharyngeal temperatures, Br J. Anaesth, 43, 673-76(1971).
Baker et al., Thermal relationship between tympanic membrane and hypothalamus in conscious cat and monkey, J Apply Physiol, 32, 739-42 (1972).
Mellegard et al., Epidural temperature and possible intracerebral temperature gradients in man, Br J Neurosurg, 4, 31-8 (1990).
Hayward et al., A comparative study of the role of the cerebral arterial blood in the regulation of brain temperature in five mammals, Brain Res, 16, 417-40 (1969).
Hirashima et al., Intracerebral temperature in patients with hydrocephalus of varying aetiology, J. Neurol Neurosurg Psychiatry, 64, 792-94 (1998).
Karaszewski, Bartosz, Early brain temperature elevation and anaerobic metabolism in human acute ischemic stroke, 132; 955-964 (2009).
Clifton, Is keeping cool still hot? An update on hypothermia in brain injury, Current Opinion in Critical Care, 10(2):116-9 (Apr. 2004).
M. Zhu et al., Improved Calibration Technique for in Vivo Proton MRS Thermometry for Brain Temperature Measurement, Magn. Reson. Med. 60(3):536-541 (Sep. 2008).
Clifton et al. Lack of effect of induction of hypothermia after acute brain injury, New England Journal of Medicine Feb. 22, 2001;344(8):556-63.

(56) References Cited

OTHER PUBLICATIONS

Minamisawa et al., Preservation of brain temperature during ischemia in rats, Journal of American Heart Association, Stroke, 21, 87-91 (1990).
Public Press Release published by EurekAlert entitled Researchers develop device to measure brain temperature non-invasively (May 2, 2011) available at http://www.eurekalert.org/pub_releases/2011-05/chot-rdd050211.php.
H. Wang et al., Rapid and selective cerebral hypothermia achieved using a cooling helmet, J. Neurosurg, 100:272-277 (Feb. 2004).
International Search Report dated Nov. 23, 2011.
Supplementary European Search Report issued in corresponding EP Application No. 11804201 on Jun. 30, 2014.

\* cited by examiner

THERAPEUTIC BRAIN COOLING SYSTEM AND SPINAL CORD COOLING SYSTEM

CROSS REFERENCE TO RELATED APPLICATION

This application claims the benefit of U.S. Provisional Application 61/359,476, filed Jun. 29, 2010.

FIELD OF THE INVENTION

This disclosure pertains to protective headgear (such as a helmet which can act as a brain cooling system and a spinal cord cooling system), device or mechanism to be used in conjunction with helmets in particular to ameliorate the long-term consequences of hypoxic-ischemic or traumatic brain injury and spinal cord injury. The drop in temperature has to be comparatively slow, i.e., less than about 0.5° C./hr in order to prevent cardiac arrhythmias and maintain blood homeostasis.

BACKGROUND

The skull is hard and inflexible, while the brain is soft with the consistency of gelatin. The brain is encased inside the skull. The movement of the skull through space (acceleration) followed by the rapid discontinuation of this action when the skull meets a stationary object (deceleration) causes the brain to move inside the skull. The brain moves at a different rate than the skull, and different parts of the brain move at different speeds because of their relative lightness or heaviness. The differential movement of the skull and the brain when the head is struck results in direct brain injury, due to diffuse axonal shearing, contusion and brain swelling.

The helmet of the present invention relates to all types of helmets. One type of helmet is a military helmet, which is a helmet utilized by military personnel in combat. The military helmets currently in use have a Kevlar or projectile resistant shell that have a number of non-functionally-interconnected pads to hold the helmet in place. The pads are made from a visco-elastic, high-energy absorption foam. While it provides protection from a diverse range of extraneous insults to the head, it cannot prevent deceleration (i.e., diffuse axonal injury) or other types of projectile injuries (e.g., bullet that perforates the helmet).

Under healthy conditions, the average or mean brain temperature (about 38° C.) exceeds body-core temperature (about 37.5° C.) by about 0.2° C. to about 0.5° C. The "core temperature" refers to the temperature of the deep tissues of the body. This temperature is maintained with minimal fluctuations by a range of autonomic/endocrinological adjustments, which are effective under normal conditions. The temperature control may fail under pathological conditions, including fever and hyperthermia, which are defined herein as different entities.

Fever is part of the body's defense mechanism against viruses or bacteria, where the hypothalamus, which behaves like a thermostat and is the primary organ that regulates temperature in the body, loses its ability to properly sense the temperature. This allows shivering to occur, which generates extra heat, in order to stimulate the efficacy of the immune system. Having a temperature increase, in the absence of brain or spinal cord injury, helps the body fight infection-mediated illness.

In contrast, hyperthermia is an elevated body temperature that occurs independently of body infection and may become a medical emergency requiring immediate treatment to prevent disability or death. The most common causes are heat stroke, adverse reactions to drugs and malignant hyperthermia (following anesthesia by halothane). Focal and regional, as opposed to systemic, increases in brain temperature are also observed following traumatic brain injury and stroke.

The opposite of hyperthermia is hypothermia, which occurs when an organism's core temperature drops below 36° C. or the temperature required for normal body functions. Hypothermia can be induced systemically or focally by exposure to cooling agents.

Brain temperature exceeds body-core temperature by 0.2° C.-0.5° C. ("core temperature" may be extrapolated from the bladder or rectal temperature). Maintaining a constant core temperature, or preventing an increase in temperature, following a variety of brain insults, is not enough to antagonize the development of long-term lesions. At present, the neuroprotective properties of mild hypothermia (defined here as reflecting a brain temperature between 33° C. and 36° C.) have been demonstrated in numerous studies. Mild hypothermia is one of the most effective neuroprotective therapies against brain ischemia and trauma that currently exists. Preliminary clinical studies have shown that mild hypothermia can be a relatively safe treatment. The feasibility of using mild hypothermia to treat stroke and spinal cord injury patients has been evaluated in various clinical trials. Increasing emphasis is being placed on developing techniques and protocols to ensure rapid cooling of patients. One of the greatest obstacles in moving the application of brain cooling hypothermia from the hospital setting to the field (e.g. war/civilian) has been the availability of adequate cooling techniques.

Generalized hypothermia was initially achieved by surface cooling, which sometimes meant submerging the neurosurgical patient in iced water while the patient was on the operating table. This method of cooling was unwieldy and required prolonged anesthesia. More recently, the feasibility of active core cooling to 32° C. using an extracorporeal heat exchanger was performed in patients with severe head injuries. At the present time, systemic surface cooling is a widely used method to induce brain systemic hypothermia using water-circulating blankets.

As cooling devices and methods are improved and proven to be effective, more data concerning the effect of temperature reduction on injury and illness recovery should be forthcoming.

To prevent shivering after heat reduction, the hypothermia-treated patient should be sedated. Both clinicians and basic scientists remain optimistic that over this decade hypothermia will emerge as a major effective therapeutic advance for patients with acute neurologic injury. However, an effective, simple hypothermic apparatus for field use remains to be developed. For example U.S. Pat. Nos. 6,969,399; 7,056,334; 7,077,858; 7,087,075; 7,179,279; 7,303,579; 6,986,783; 7,056,282 and U.S. Patent Pub. No. 2010/0211140 all disclose cooling techniques and systems; however, none of these systems are suitable for use in non-hospital settings. Moreover, for mild hypothermia to be effective, studies have shown that it must be induced within four hours of injury. See Clifton et al., *Lack of effect of induction of hypothermia after acute brain injury*, New England Journal of Medicine 2001 Feb. 22; 344(8):556-63; Clifton, *Is keeping cool still hot? An update on hypothermia in brain injury*, Current Opinion in Critical Care, 10(2): 116-9 (April 2004).

Therefore, a need exists for developing an effective, simple hypothermic apparatus for mobile use such as in a field setting. The helmet can used by soldiers in war or by civilians. The helmet use will selectively and uniformly lower a user's brain temperature slowly in a controlled manner so as to avoid the risks associated with rapid induction of hypothermia. It would be highly desirable to provide an effective, controlled mechanism, that can be triggered by third parties immediately following brain injury, that has the effect of preventing the increase in intracranial pressure, swelling and acute and long-term damage. To effectively achieve these goals, the apparatus would need to be effective without removing the patients existing clothing, including war/civilian helmets. For example U.S. Pat. Nos. 4,552,149; 4,753,242; 5,261,399; 5,539,934; 5,871,526; 5,913,885; 5,957,964; 6,030,412; 6,126,680; 6,183,501; 6,277,143; 6,312,453; 6,416,532; 6,461,379; 6,682,552; 6,962,600 and 7,846,118 disclose hats, wraps, covers, etc. for cooling body temperatures; however, all of these systems would require removing the patient's current helmet or clothing in the field, which could exacerbate the patient's condition or, in the case of combat use, leave the patient vulnerable to further attack. In addition, the system would need to be highly mobile and be incorporated into the user's current equipment, meaning that the system or apparatus would not obstruct the user, impair the functioning of the user's current equipment, or be susceptible to failure resulting from incidental damage prior to activation as could occur in other such systems. See U.S. Pat. Nos. 4,691,762; 7,008,445; 7,052,509; 7,507,250; 7,565,705 and 7,621,945.

SUMMARY OF THE INVENTION

The present invention relates to a hypothermic helmet for protection of a wearer's brain. The hypothermic helmet has one or more inflatable pads or caps, which may be interconnected, attached inside the helmet body. The system also has at least one canister or container containing different cooling gases, and at least one temperature-sensitive probe capable of determining the wearer's brain temperature, which may be displayed through a color indicative gauge with variable colors or a digital reader, for temperature monitoring. One or more bi-directional pressure-sensitive valves are positioned on the helmet for receiving the canister, which inflates the interconnected pads and cools a wearer's brain in a controlled manner (at a rate of about 0.1° C. to about 0.5° C./hour) to between about 33° C. and about 36° C. Additionally, an inflatable collar enhances the induction of brain cooling by decreasing the temperature of the arterial blood passing through the neck. One or more bi-directional pressure-sensitive valves are positioned on the collar for receiving the canister filled with cooling gas. A face-mask, visor and thermo-insulating hood may also be attached to the helmet and may be used in conjunction into the collar to create a temperature barrier.

Another embodiment relates to a hypothermic helmet for protection of a wearer's brain and/or spinal cord. The hypothermic helmet comprises one or more inflatable pads, which may be interconnected. The hypothermic helmet may comprise one or more inflatable spinal cord straps. At least one canister or container containing different cooling gases and at least one temperature-sensitive probe capable of determining temperature for temperature monitoring are also included. The helmet is capable of cooling the user's brain to a mean temperature of about 33° C. to about 36° C. within about 24 hours and is capable of maintaining the temperature of the user's brain within the range for about 24 hours to about 96 hours.

In another embodiment, this disclosure relates to a brain cooling system and spinal cord cooling system, device or mechanism for use in military helmets, which refer to helmets used in combat. In another embodiment, this disclosure relates to use in non-military helmets, which are helmets used in non-combat scenarios. The brain cooling system comprises an inflatable pad, or a set of interconnected pads, attached to the interior surface of a helmet body, together with a series of valves that allow cooling gases to be delivered from a high pressure canister. The spinal cord cooling system includes one or more, e.g., one, inflatable straps attached to the bottom of the helmet body, together with a series of valves that allow cooling gases to be delivered from a high pressure canister. The brain and spinal systems may be joined at a collar located at a user's neck. The collar further enhances the induction of brain cooling by decreasing the temperature of the arterial blood passing through the neck. The use of different cooling gases permits a controlled lowering (at a rate of about 0.1° C. to about 0.5° C.) of the brain to a temperature to about 33° C., which is about 2.5° C. to 4.5° C. below the core temperature (about 37.5° C.). The brain and spinal cord cooling systems are thermostatically monitored by inclusion of a temperature-sensitive probe, permitting adjustment of the temperature when necessary.

Maximum pressure inside the system (e.g., the helmet and collar) is controlled by one or more, e.g., three, individual bi-directional pressure-sensitive valves. The availability of the alternative valves avoids the need to move the injured head to implement the cooling mechanism and/or provides optional gas flow rates through the calibration of the individual bi-directional pressure-sensitive valves. Additional features of the system include a visor, face mask and hood which are attached to the helmet body, and which, when combined, create a temperature barrier after the cooling system has been implemented.

The military helmet comprises: a plurality of inflatable interconnected pads receiving hook and loop type fasteners of either hook type or loop type; the helmet body having a plurality, including but not limited to about 6 to about 10, inflatable interconnected pads between a wearer's head and the helmet body, where the inflatable interconnected pads are made from a breathing elastic material in contact with a wearer's skin, and will accommodate an expandable gas-filled balloon. Additionally, at least one canister and/or container containing different cooling gases and one or more bi-directional pressure-sensitive valves that allow the controlled release of pressure are included. The inflatable interconnected pads are capable of being inflated with gas released from the container inserted into one of the bi-directional pressure-sensitive valves positioned at the top and lateral sides of the helmet body, which are connected to the plurality of inflatable interconnected pads. The temperature-sensitive probe is connected to a gauge, which can be used to monitor the temperature. The brain cooling system may also include an inflatable collar, which enhances the induction of brain cooling by decreasing the temperature of the arterial blood passing through the neck. One or more bi-directional pressure-sensitive valves are positioned on the collar for receiving the canister filled with cooling gas.

Another embodiment relates to a replacement brain cooling system kit for an military helmet or civilian helmet. The kit has a plurality of inflatable interconnected pads fastened to the military helmet by any means known in the art, including, but not limited to, receiving hook and loop type fasteners of either hook type or loop type. The helmet body has one or more inflatable interconnected pads between a wearer's head and the helmet body. The inflatable interconnected pads are made from an elastic material, which may be in contact with a wearer's skin and will accommodate an expandable balloon, which may be gas-filled. Additional interconnected pads and fasteners may be incorporated into an inflatable collar.

Another embodiment relates to the helmet comprising an inflatable head-band connected to one or more valves, with the inflatable head-band performing like an air-bag. The helmet may have about 2 to about 8 cushion pads attached, which are positioned peripherally to permit inflation of the head-band. One or more bi-directional pressure-sensitive valves allow the controlled release of pressure from at least one canister and/or container inserted into one or more bi-directional pressure-sensitive valves positioned at the top and lateral sides of the helmet body, which are connected to the inflatable head-band. Additional inflatable head-bands, cushion pads and pressure-sensitive valves may be incorporated into an inflatable collar.

Another embodiment relates to a brain and spinal cord cooling system comprising an inflatable crown cap and an inflatable strap capable of being inflated with gas released from a source such as a canister inserted into one or more bi-directional pressure-sensitive valves positioned at the top, middle or bottom of the strap or adjacent collar.

In addition, an embodiment of this invention relates to a method of conferring the benefits of an immediate, but controlled, hypothermic assistance in the event of acute brain and/or spinal cord injury. One embodiment provides a method of adapting a helmet body to incorporate a brain cooling system comprising the steps of incorporating a plurality of inflatable interconnected pads into a helmet body, incorporating one or more bi-directional pressure-sensitive valves into the helmet body, connecting said valves to the inflatable interconnected pads, connecting at least one canister containing cooling gases to said valves, inflating said inflatable interconnected pads with the cooling gases, and monitoring at least one temperature-sensitive probe to determine a user's brain temperature. A face-mask, visor, thermo-insulating hood and/or collar may also used to create a temperature barrier. A better prognosis is expected if mild to moderate hypothermia is maintained for an extended period of up to four hours and/or until the patient is transferred from the scene of the incident to the closest medical facility.

Further objects, features and advantages of the present disclosure will be understood by reference to the following drawings and detailed description.

DETAILED DESCRIPTION

Figure 1:
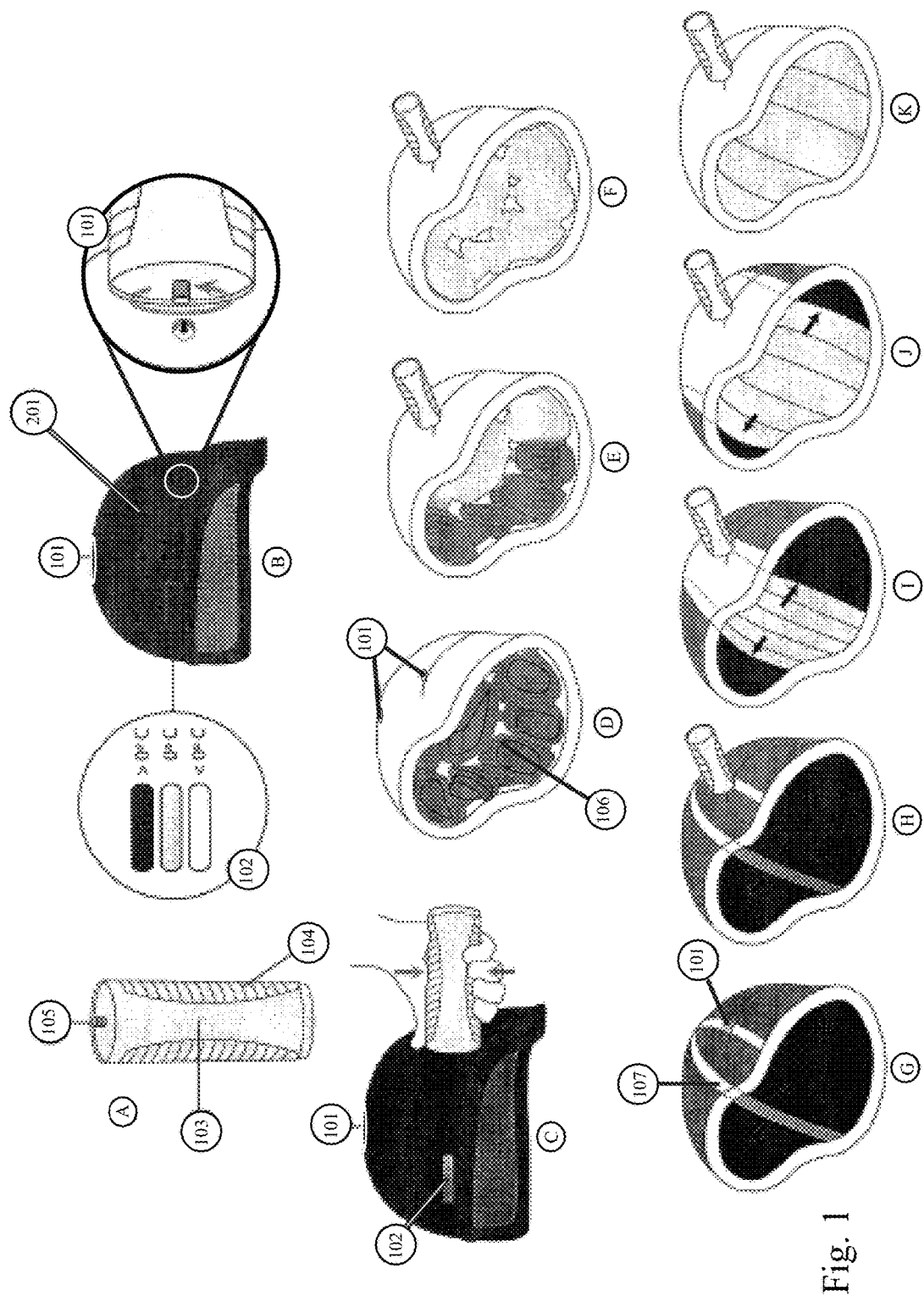
FIG. 1 A-K diagrammatically shows a military helmet brain cooling system of this disclosure.

The present invention relates to a brain cooling system comprising a helmet. In one embodiment, the helmet can be for use in military helmets or in non-military helmets. The brain cooling system comprises an inflatable pad, or a set of inflatable interconnected pads, attached to the interior surface of the helmet body, together with a series of valves that allow coolants, including, but not limited to, pressurized liquids or gases to be delivered from a high pressure canister. The use of different coolants, or cooling gases, achieves (at a rate of about 0.1° C. to about 0.5° C./hour) mild (about 36° C.) or moderate (about 33° C. to about 35° C.), brain hypothermia, which is about 2.5° C. to about 4.5° C. below the normal range of brain temperature which ranges from about 37.5° C. to about 38.0° C. The brain cooling system is thermostatically monitored by the inclusion of a temperature-sensitive probe and temperature display. The display may be a color indicator gauge, which displays variable colors permitting the adjustment of the cooling temperature when necessary.

The present invention may also include a collar that enhances the induction of brain cooling by decreasing the temperature of the arterial blood passing through the neck. The collar may contain one or more bi-directional pressure-sensitive valves that may be positioned for receiving a coolant filled canister. The collar may also have various structural components such as the inflatable pads or other features found throughout the rest of the present invention or accessories such as buttons, shoulder pads, collar stiffeners and zip fasteners. In addition, the collar may have various structural properties such as being inflatable or non-inflatable, hollow or can include rigid components, such as metal, rubber, plastics or other materials. Production of the collar as well as the helmet is well within skills of one of ordinary skill in the art of device development. The collar can be made of an assortment of materials including, but not limited to, breathable elastic materials or polymers such as nylon, dacron, mylar, spandex, kevlar or nomex.

The present invention uses coolants, typically in the form of pressurized gas to cool the brain temperature. Various gases and liquids, or mixtures thereof, are anticipated to be used with this system including, but not limited to, known coolants such as nitrogen, carbon dioxide or inert gases such as Helium. The liquid coolants may include a perfluorocarbon, including, but not limited to, perfluorohexane, perfluoropentane, or 2-methyl-perfluoropentane; refrigerants, including, but not limited to halomethanes, haloalkanes and anhydrous ammonia; and nanofluids, including, but not limited to alumina, titanium dioxide, carbon nanotubes, silica, or metals in a carrier liquid.

The coolant is distributed throughout the system through the use of pressurized valves and tubes. Maximum pressure inside the system is controlled by one or more, e.g., three, individual bi-directional pressure-sensitive valves. The availability of the alternative valves avoids the need to move the injured head to implement the cooling mechanism. The system of the present invention may contain one or more bi-directional pressure-sensitive valves which permit varying amount of gas flow into the inflatable pads. Additional features of the brain cooling system may include a visor, face mask and hood, which are attached to the helmet body, and which, when combined with the helmet, create a temperature barrier after the cooling system has been implemented, in order to permit the maintenance of therapeutic cooling of the brain for up to about 12 hours, about 24 hours, about 48 hours or about 96 hours. Such maintenance of the brain cooling is usually achieved in a hospital setting after stabilizing the patient.

The gas or fluid delivery system of this invention includes delivering a fixed, or substantially fixed, ratio of liquid and gas. The delivery system is highly mobile and can be adjusted to particular gas flow rates through the use of bi-directional, pressure sensitive valves. As gas is delivered to the helmet, gas will flow from a reservoir or bottle in the canister through the pressurized value. The gas or pressurized liquid may further flow through a series of gas lines incorporated into the inflatable pads and/or helmet. Gas lines may also comprise single or branched tubes. As the reservoir becomes de-pressurized upon connection to the pressurized value, the contents of the reservoir will flow through the line and into the inflatable pads. The flow rate of the coolant will directly depend on the pressure of the gas being delivered from the reservoir or canister, i.e., higher gas pressure will result in a faster flow rate. Therefore, a fixed or preset rate of liquid or gas can be delivered to the helmet upon use.

Flow restrictions may also be incorporated into the helmet or the gas delivery systems of the helmet. For example, flow restrictors may allow particular inflatable pads to be closed off from adjacent inflatable pads or sections of an inflatable crown or cap. This is particularly useful if a section has been damaged prior to use. Flow restrictors can be pressure-sensitive based on the ambient pressure of the inflatable pads prior to use. Stopcocks may also be connected to the gas lines in between inflatable pads to direct flow either to restrictors or to stop liquid flow altogether. Pressurized filters may also be used, ensuring that any inflatable pad is not over-pressurized resulting in the failure of the pad. Activation of the overpressure safety device may switch the pressure-sensitive valves to stop gas flow and vent the gas line(s) or particular inflatable pad(s).

The fluid control reservoir or canister may be rated to withstand the pressure of the compressed gas, for example the fluid control canister may be a poly ethylene terephalate (PET) container tested to pressures in excess of 100 psi, 150 psi or 200 psi. In addition, a burst disk or relief valve, set at a value exceeding the expected operating pressure, for example, 60 to 90 psi, may be added to the container as a safety means for venting gas in the event of over pressurization. The container may further contain a flow meter allowing a user to observe the flow rate of the gas or liquid as it leaves the canister. The operator may be able to adjust the flow rate into the helmet through the use of different pressure-sensitive valves, each geared for a specific amount of pressure, through alterations to the canister, or through any other means known in the art.

The helmet of the brain cooling system is designed to cool the brain at a controlled rate over a specific amount of time to a specific mean temperature. As used herein, the term controlled may mean constant, i.e., does not vary over time where the time period can be controlled to be as short or as long as needed. Overall, different controlled rates may be used with the same patient. The rate of cooling may be linear or non-linear. Treating a patient using the helmet will also require re-warming the brain at a controlled rate of about 0.1° C. to about 0.3° C./hour from times ranging from about 24 to about 72 hours, or until a mean temperature of the brain is about 37.5° C. The rate of warming may be linear or non-linear. The helmet is capable of providing a cooling rate to the brain ranging from about 0.1° C. to about 0.5° C./hour, about 0.1° C. to about 0.4° C./hour, about 0.1° C. to about 0.3° C./hour, about 0.1° C. to about 0.2° C./hour, about 0.2° C. to about 0.4° C./hour, about 0.2° C. to about 0.3° C./hour or about 0.3° C. to about 0.5° C./hour.

The time required to meet a mean temperature in the brain of about 33° C. may range from about 12 hours to about 18 hours. The mean temperature may be achieved using the helmet, or alternatively using the helmet in conjunction with advanced medical facilities, such as hospital. Other higher mean temperatures in the brain may be achieved in shorter time periods ranging from immediately after the insult to the brain to about 2 hours depending on the rate of cooling. An intravenous saline solution which is maintained at temperatures ranging from about 4° C. to about 5° C. in quantities such as 0.5, 1.0 and 1.5 liters may be provided to a patient to aid in cooling of the brain.

The mean temperature of the brain after hypothermia induction will usually be lower than the core body temperature. The mean temperature of the brain after hypothermia induction may range from about 33° C. to about 36° C., about 34° C. to about 37° C., about 33.5° C. to about 36.5° C., about 34° C. to about 36° C., about 35° C. to about 36° C., about 32° C. to about 35° C. or about 32° C. to about 33° C.

The mean temperature of the brain may be maintained for an extended period such as about 24 hours to about 96 hours, about 36 hours to about 72 hours, about 48 hours to about 56 hours, or about 48 hours. The temperature may be maintained using the helmet or alternatively the helmet in conjunction with advanced medical facilities.

The sensitivity, i.e., the resultant temperature change, and/or the resultant rate of temperature change, experienced by the patient, will depend on the physical conditions of the patient, e.g., the size and age of the patient. Furthermore, calculations can be done to determine how cold the head might become if all the cooling is focused solely in the head. The amount of cooling to the head can be calculated using the following assumptions: (1) mass of brain, for example, 1.4 kg, (2) specific heat of water and (3) heat transfer from body (warming from cerebral blood flow) is negligible. Heat load calculation is an important part of sizing and designing a radiant heating/cooling system. There are two types of heat loss to consider: conduction and convection.

Calculations—Calculate $\Delta T$. For example, $\Delta T$ is a difference between brain core temperature (38° C.) and brain surface temperature (37.5° C.). $\Delta T = 0.5$° C. Brain weight: 1.4 Kg (75% water), Blood flow: 1.25 liters/min, Brain volume: 1,400 cc (cm$^3$).

A typical brain heat load calculation consists of surface heat loss calculation through convection and heat loss due to blood flow (i.e., conduction). The helmet modulates the extent of heat loss mainly by conduction. We calculated $\Delta T$ using the Fourier law:

$$q'' = \frac{q}{A} = -k\frac{\partial T}{\partial x}.$$

taking in consideration the physical "barriers" which slow down or resist heat transfer from the brain (e.g., empty spaces between the head and the helmet). Brain heat loss vs. rewarming by systemic blood flow (37° C.): The mass of circulating blood within the brain per minute is similar to the brain mass. The amount of heat to be removed from the brain in order to drop in 1° C. the brain temperature:

$Q = m \cdot c \cdot \Delta T$ $m = 1.4$ kg $c = 1$ kcal/kg/C (considering specific heat of water)

Thus, it will take 1400 calories for each 1° C. drop. Energy provided by brain blood flow: Considering 1.25 liters/min, $\Delta T$ of 1° C. and 30 min of perfusion (i.e., within 30 min~37 liters or 37 Kg)—there is a need of 37,500 calories for each 1° C. drop—or a continuously removal of 75 kcal/h to drop the blood temperature in 1° C.

The brain may then be warmed at a rate ranging from about 0.1° C. to about 0.3° C./hour, about 0.1° C. to about 0.2° C./hour or about 0.2° C. to about 0.3° C./hour. The time required to re-warm the brain may range from about 24 hours to about 96 hours, about 36 hours to about 72 hours, about 48 hours to about 56 hours, or about 48 hours. Re-warming of the brain is typically handled in the clinical setting.

The rate of cooling provided by the coolant may be determined through any means known in the art. The following calculations estimate the maximum cooling that can be obtained using a liquid coolant; however, it should be understood that similar calculations can be used to determine the rate of cooling for other coolants.

The cooling effect is related to two aspects of thermodynamics: (1) heat capacity of the liquid, as it is warmed from its temperature at application to that of the body, and (2) heat of vaporization as it changes from the liquid to the gas state. See U.S. Patent Pub. No. 2010/0211140. The relevant properties of a particular liquid are: p (Density), c (Specific Heat) and h (Latent Heat).

The calculation for heat transfer due to warming the liquid is: $Q = c^* m^* (T_2 - T_1)$ or $Q = cm\Delta T$ (where m=the mass of the liquid administered, $T_1$ is the temperature of the liquid at administration, and $T_2$ is the temperature to which the liquid is warmed).

The calculation for heat transfer due to evaporation of the liquid is: $Q = h^* m$.

The brain temperature may be monitored through a variety of ways, both invasively and non-invasively. As used herein the term "mean brain temperature" refers to an average (as calculated mathematically by any standard means) temperature of the brain because the temperature across the brain from the surface to the core may vary by as much as 0.5° C. under normal conditions. Accurate temperature measurements depend on the type of thermometer and where that thermometer is placed. Currently, there are numerous types of thermometers used. For example, mercury, liquid crystal display (LCD), thermocouples and thermistors, which are probes in electric thermometers that convert the electrical temperature signal into analog or digital displays and are commonly used measurement devices. In addition, zero heat flow thermometers, which combine the use of a thermistor, a heat-flow sensor, and a heater, radiotelemetry thermometers, which measure the changes in radio frequency based on temperature-dependent inductance, and infrared thermometers, which measures infrared energy emitted by the core-temperature tissues, may also be used to measure temperature.

The anterior preoptic region in the hypothalamus is the primary thermoregulatory center in mammals. In humans, the hypothalamus maintains the body temperature between 36.5° C. and 37.5° C. Initially, brain temperature was continuously monitored by placing a thermocouple into an intraventricular catheter for intracranial pressure monitoring. Mellegard et al., *A method for monitoring intracerebral temperature in neurosurgical patients*, Neurosurgery, 27, 654-57 (1990). Thermometers or thermistors may be combined with probes for measuring intracranial pressure, $pO_2$, $pCO_2$ and other metabolites, so that brain temperature can be measured continuously in the lateral ventricles or in the parenchyma. The use of these techniques has revealed regional differences in brain temperature, with deeper zones being warmer than surface structures. Hirashima et al., *Intracerebral temperature in patients with hydrocephalus of varying ethiology*, J Neurol Neurosurg Psychiatry, 64, 792-94 (1998).

The placement of the temperature probes may vary. For example, there are various placement areas for temperature monitoring, including, sublingual, axillary, rectal, tympanic, esophageal, nasopharyngeal, bladder and central venous. Brain temperature may also be monitored and at minimal risk to the patient. Mellegard et al., *Epidural temperature and possible intracerebral temperature gradients in man*, Br J Neurosurg, 4, 31-8 (1990).

The temperature of the deep brain is slightly greater than the temperature of the core during steady-state conditions. The mean difference in between the brain temperature and esophageal temperature is 1.5+/-0.75° C. at 10 cm, 0.6+/-0.63° C. at 17 cm, and 0.25+/-0.2° C. at 24 cm. This temperature gradient may be a result of the phenomenon of countercurrent exchange within the brain. See Hayward et al., *A comparative study of the role of the cerebral arterial blood in the regulation of brain temperature in five mammals*, Brain Res, 16, 417-40 (1969). The normal arterial verse jugular venous differences in blood temperature, when calculated based on $O_2$ consumption, blood flow, and heat production in healthy patients should be approximately 0.4° C. Brengelmann, *Body temperature regulation*, Textbook of Physiology, 1584-96 (1989). Because of the extensive capillary network within brain tissue, it is likely that the brain acts as a countercurrent heat exchange. As arterial blood travels deeper into the brain tissues, heat is gained, and as blood moves to more peripheral cooler tissues in the brain, heat is lost. Therefore, core temperature exists more as a physiological concept than as the temperature of a precise or tightly defined anatomic location.

Ideal sites of temperature measurements should be protected from heat loss, be painless to the patient, and be convenient for measuring. Core temperature is best measured from the pulmonary artery, distal esophagus, tympanic membrane, or nasopharynx. Oral, axillary, rectal, and bladder temperatures approximate core temperature in many clinical circumstances, except during changes in brain temperature, which may happen following traumatic brain injury or hypoxic-ischemic brain insults.

Brain temperature is determined by a number of factors, including cerebral metabolic rate, cerebral blood flow, and arterial blood temperature. Brain temperature is also influenced by the surrounding environment. Whitby et al., *Cerebral, esophageal and nasopharyngeal temperatures*, Br J Anaesth, 43, 673-76 (1976). Cerebral metabolic activity generates heat and results in a small temperature gradient (<1° C.) between deep brain temperature and that of the superficial parenchyma through which the proximal cerebral arteries course. Baker et al., *Thermal relationship between tympanic membrane and hypothalamus in conscious cat and monkey*, J Apply Physiol, 32, 739-42 (1972). Cerebral blood flow and the blood-brain temperature gradient determine the magnitude and direction of heat exchange in the brain. Id.; Hayward et al., *Role of arterial blood in the regulation of brain temperature in the monkey*, Am J Physiol, 215, 389-403 (1968). Cerebral blood flow and brain temperature are related in two ways. First, the blood flow to the brain supplies the nutrients that are necessary to generate heat through cerebral metabolism. If cerebral blood flow is reduced to limit metabolism in the brain, then brain temperature decreases as well. Minamisawa et al., *Preservation of brain temperature during ischemia in rats*, Stroke, 21, 87-91 (1990). Second, cerebral blood flow is tightly coupled to brain metabolic rate. In healthy patients, cerebral metabolism and, therefore, cerebral blood flow is altered by induced changes in brain temperature. Patients with a brain temperature exceeding 36° C. have greater cerebral blood flow values than patients with a brain temperature below 36° C.

Recently, it was shown that brain temperature may also be monitored through the use of an MMS Radiometric Sensing Transducer as suggested by Wouter Stomp, *Non-Invasively Measuring Brain Temperature*, MedGadget.com (May 31, 2011) available at http://medgadget.com/2011/05/noninvasively_measuring_brain_temperature-2.html (last visited Jun. 20, 2011), which passively detects microwave emissions produced by the brain tissue beneath the skull.

Alternatively, the brain temperature may be monitored through the use of MRS thermometry, which uses the MR frequency of water protons or the resonance of the N-acetyl-aspartate methyl groups to determine internal brain temperature as disclosed in M. Zhu et al., *Improved Calibration Technique for in Vivo Proton MRS Thermometry for Brain Temperature Measurement*, Magn. Reson. Med. 60(3): 536-541 (September 2008) and Bartosz Karaszewski, *Early brain temperature elevation and anaerobic metabolism in human acute ischemic stroke*, Brain, 132; 955-964 (2009). In MRS Thermometry, the temperature-dependent changes in hydrogen bonding cause the chemical shift of water to vary linearly with temperature at 0.01 ppm/° C., while the chemical shift of N-acetyl aspartate is independent of temperature. Both of these chemical shifts are essentially independent of pH, making MRS Thermometry a reliable method of temperature determination by comparing and contrasting the relative chemical shifts of water and the N-acetyl-aspartate methyl groups.

Furthermore, the use of Magnetic Resonance User Interface ("MRUI") for spectral quantification is advantageous because the frequency resolution of MRUI is very high as quantification is carried out in the time domain, effectively looking for small phase changes in the signals over the entire duration of the free induction decay. Therefore, frequency resolution is determined by the Cramer-Rao bounds and not by the apparent digital resolution of the spectra, giving better determination of any chemical shifts.

One embodiment of the invention relates to a brain cooling system that is a spinal cord cooling system for cases of spinal cord contusion. The spinal cord cooling system includes the above components of the brain cooling system and additionally one or more, e.g., one, inflatable straps attached to the bottom of the helmet body. The brain cooling system and spinal cord cooling system may further comprise an assortment of inflatable pads situated throughout the system so as to provide uniform cooling of the brain and spinal cords, including the frontal, parietal and occipital lobes, occipital bone and vertebrae.

Another embodiment of the invention relates to an military helmet which has a plurality of inflatable interconnected pads receiving hook and loop type fasteners of either hook type or loop type. The system comprises a helmet body with preferably about 6-10 hollow cushion pads between the head and the helmet body. The hollow pads are made from a breathing elastic material in contact with the skin of a wearer, and will accommodate an expandable gas-filled balloon. The system may incorporate any type of fastener, including, but not limited to, glue, buttons or other fasteners known in the art. The inflatable interconnected pads can be inflated with gas released from one or more canisters inserted into valves positioned at the top and lateral sides of the body of the helmet, which are connected to the pad system and avoids the need to move the injured head to implement the cooling mechanism. The valves are bi-directional, allowing the controlled release of pressure. Additional features of the military helmet include a visor, face mask and hood. These components can be attached to the military helmet after the cooling is implemented and positioned to insulate the head, and to prevent loss of cooling and a concomitant increase in brain temperature.

The brain cooling system of the present invention may also include an inflatable collar, which enhances the induction of brain cooling by decreasing the temperature of the arterial blood passing through the neck. One or more bi-directional pressure-sensitive valves may be positioned on the collar for receiving the canister filled with cooling gas.

Another embodiment of the invention relates to a replacement military helmet. The kit comprises a plurality of inflatable interconnected pads receiving hook and loop type fasteners of either hook type or loop type, to be attached to the helmet body with about 6-10 hollow cushion pads between the head and the helmet body. The hollow pads are made from a breathing elastic material for contacting the skin of a wearer, and to accommodate an expandable gas-filled balloon. Additional features of the military helmet replacement kit include a visor, a face mask and hood. These components are attached to the military helmet after the cooling is implemented and positioned to insulate the head and prevent the loss of cooling and a concomitant increase in brain temperature. Additional hollow pads and fasteners may also be incorporated into an inflatable collar.

Other embodiments of the invention relate to a military helmet brain cooling system having a single inflatable head-band connected to multiple, e.g., three, valves which can perform or function as an air-bag. The valves are positioned at the upper middle and at each lateral side of the helmet body. In this formulation, the helmet body has about 2-8 cushion pads attached, which are positioned peripherally to permit inflation of the head-band, delimiting the area of expansion of the fully-inflated gas-cooled pad. The valves are bi-directional, allowing the controlled release of pressure. The multiple, e.g., three, valves are aligned along the head-bag avoiding the need to move the injured head in order to implement the cooling mechanism. Additional features of the military helmet include a visor, a face mask and hood. These components are attached to the military helmet after the cooling is implemented and positioned to insulate the head, and to prevent loss of cooling and a concomitant increase in brain temperature. Additional head-bands, pads or values may be incorporated into an inflatable collar attached to the system.

Another embodiment of the invention relates to a replacement military helmet air-bag kit. The kit comprises a single inflatable head-band connected to multiple, e.g., three, valves, performing like an air-bag. The valves are positioned at the upper middle and at each lateral side of the helmet body.

Another embodiment of the invention comprises a non-military helmet brain cooling system having a single inflatable crown cap attached to an helmet body and connected to up to three valves. The valves are positioned at the upper middle and at each lateral side of the helmet body, avoiding the need to move the injured head in order to implement the cooling mechanism. The valves are bi-directional, allowing the controlled release of pressure. Additional features of the non-military helmet brain cooling system include a visor, a face mask and hood. These components are attached to the non-military helmet after the cooling is implemented and positioned to insulate the head and prevent loss of cooling and a concomitant increase in brain temperature. The brain cooling system may also include an inflatable collar, which enhances the induction of brain cooling by decreasing the temperature of the arterial blood passing through the neck. One or more bi-directional pressure-sensitive valves may be positioned on the collar for receiving the canister filled with cooling gas.

Another embodiment of the invention relates to a replacement non-military helmet brain cooling system crown cap kit. The kit comprises a single inflatable crown cap connected to multiple, e.g., three, valves. The valves are positioned at the upper middle and at each lateral side of the helmet body. Additional features of the replacement non-military helmet brain cooling system crown cap kit include a visor, a face mask, hood and collar.

One embodiment of the invention relates to a non-military helmet brain cooling system having a single inflatable head-band connected to multiple, e.g., three, valves, performing like an air-bag. The valves are positioned at the upper middle and at each lateral side of the helmet body. In this formulation, the helmet body has about 2-8 cushion pads attached, which are positioned peripherally to permit inflation of the head-band, delimiting the area of expansion of the fully-inflated gas-cooled pad. The valves are bi-directional, allowing the controlled release of pressure. The multiple, e.g., three, valves are aligned along the head-band avoiding the need to move the injured head to implement the cooling mechanism. The optional visor attached to the non-military helmet after the cooling is implemented helps to prevent loss of cooling and a concomitant increase in brain temperature.

In addition, this embodiment may include a replacement brain cooling system air-bag kit. The kit comprises an inflatable head-band connected to multiple, e.g., three, valves, performing like an air-bag. The valves positioned at the upper middle and at each lateral side of the helmet body. In addition, the kit may include head-band replacements adapted for use in an adjoining collar or spinal cord cooling system.

Where neck injury is associated with a spinal cord contusion, this disclosure relates to a spinal cord cooling system with at least one inflatable strap. The spinal cord cooling system comprises a strap, which may be attached to the back of an military helmet or to the non-military helmet body, and that accommodates a single, expandable gas-filled cushion. The strap may be incorporated into an inflatable collar. The inflatable strap may be inflated with gas released from canisters inserted into one of the bi-directional valves positioned at the top, middle or bottom sides of the body of the strap, avoiding the need to move the injured neck or spinal cord in order to implement the cooling mechanism. The valves are bi-directional, allowing the controlled release of pressure. Additional features of the spinal cord cooling system include a set of parachute-like straps, which are attached to the body of the patient to properly position and stabilize the hypothermic system.

One embodiment of the invention relates to a military helmet brain cooling and spinal cord cooling system having a plurality of inflatable interconnected pads receiving hook and loop type fasteners of either hook type or loop type. The military helmet and spinal cord cooling system comprises a helmet body with preferably about 6-10 hollow cushion pads between the head and the helmet body. The hollow pads are made from a breathing elastic material in contact with the skin of a wearer, and will accommodate an expandable gas-filled balloon. The inflatable interconnected pads can be inflated with gas released from one or more canisters inserted into valves positioned at the top and lateral sides of the body of the helmet, which are connected to the pad system. The military helmet and spinal cord cooling system can include an inflatable strap attached to the back of the helmet body for contact with a wearer's skin along the spinal cord. The inflatable strap is capable of being inflated with gas released from the at least one canister and/or container inserted into the one or more bi-directional pressure-sensitive valves positioned at the top, middle or bottom of the strap. This avoids the need to move the injured head to implement the cooling mechanism. The valves are bi-directional, allowing the controlled release of pressure.

One embodiment of the invention relates to a replacement military helmet and spinal cord cooling system kit. The kit comprises a plurality of inflatable interconnected pads receiving hook and loop type fasteners of either hook type or loop type, to be attached to the helmet body with about 6-10 hollow cushion pads between the head and the helmet body. The hollow pads are made from a breathing elastic material for contacting the skin of a wearer, and to accommodate an expandable gas-filled balloon. The military helmet and spinal cord cooling system kit includes an inflatable strap for attachment to the back of the helmet body. The inflatable strap contacts a wearer's skin along the spinal cord.

One embodiment of the invention relates to a military helmet and spinal cord cooling system having a single inflatable head-band connected to multiple, e.g., three, valves, performing like an air-bag. The valves are positioned at the upper middle and at each lateral side of the helmet body. In this formulation, the helmet body has about 2-8 cushion pads attached, which are positioned peripherally to permit inflation of the head-band, delimiting the area of expansion of the fully-inflated gas-cooled pad. The military helmet and spinal cord cooling system includes an inflatable strap attached to the back of the helmet body for contact with a wearer's skin along the spinal cord. The inflatable strap is capable of being inflated with gas released from the at least one canister and/or container inserted into the one or more bi-directional pressure-sensitive valves positioned at the top, middle or bottom of the strap. The valves are bi-directional, allowing the controlled release of pressure. The multiple, e.g., three, valves are aligned along the head-bag avoiding the need to move the injured head in order to implement the cooling mechanism.

One embodiment of the invention relates to a replacement military helmet and spinal cord cooling system air-bag kit. The kit comprises a single inflatable head-band connected to multiple, e.g., three, valves, performing like an air-bag. The valves are positioned at the upper middle and at each lateral side of the helmet body. The military helmet and spinal cord cooling system kit includes an inflatable strap for attachment to the back of the helmet body. The inflatable strap contacts a wearer's skin along the spinal cord.

Another embodiment relates to a non-military helmet and spinal cord cooling system having a single inflatable crown cap attached to an helmet body and connected to up to three lateral side of the helmet body, avoiding the need to move the injured head in order to implement the cooling mechanism. The non-military helmet and spinal cord cooling system includes an inflatable strap attached to the back of the helmet body for contact with a wearer's skin along the spinal cord. The inflatable strap is capable of being inflated with gas released from the at least one canister and/or container inserted into the one or more bi-directional pressure-sensitive valves positioned at the top, middle or bottom of the strap. The valves are bi-directional, allowing the controlled release of pressure.

The disclosure will be further described with reference to the accompanying drawings, by way of example and without intending to be limiting.

FIG. 1 diagrammatically shows one form of the apparatus or helmet of the disclosure comprising an military helmet having a plurality of inflatable interconnected pads 106. The military helmet includes a helmet body 201 with 6-10 hollow cushion pads 106 between the head and the helmet body 201. The hollow pads 106 accommodate an expandable gas-filled balloon as shown in FIG. 1 D-F. The inflatable interconnected pads 106 are inflated with gas released from canister 103 inserted into valve 101 positioned at the top and lateral sides of the helmet body 201, which are connected to the pad system 106. The valves 101 are bi-directional, allowing the controlled release of pressure. The brain cooling system is thermostatically monitored by inclusion of a temperature-sensitive probe connected to a color indicative gauge 102, which displays variable colors. The skilled artisan will understand that the invention is not limited to a specific method of temperature monitoring and that the invention encompasses any technique known in the art, including, but not limited to, non-invasive procedures such as monitoring radiation emitted in the microwave spectrum.

$CO_2$ (or other gases) can be included in the cartridge or canister 103 that allows rapid inflation of interconnected pads 106 as shown in FIG. 1 C-F, or head-band 107 as shown in FIG. 1 G-K. The gas may be released by lateral compression of an aluminum container 103 as shown in FIG. 1 C. The gas produces an endothermic reaction. In order to release the gas, in one embodiment, the nozzle of the cartridge/canister/can 105 is manually screwed clockwise into the valve 101 as shown in FIG. 1 B insert, allowing fast inflation and cooling of the interconnected pads 106 or of the head-band 107. The interconnected pads 106 or the head-band 107 perform like an air-bag as diagramed in FIG. 1 after screwing the nozzle 105 of the can 103 into a valve 101 positioned on the helmet body 201.

The dynamics of filling the pads 106 or head-band 107 is illustrated by arrows placed inside the respective helmets and by replacing areas of dark color with light gray as shown in FIG. 1 D-K. The canister 103 may have a clockwise orientation, with the valves 101 and canister nozzle 105 threaded for a clockwise rotation as the supination of the arm, which is generally used by a right-handed person to turn the canister 103 by gripping the grip 104 as screwing clockwise, is generally stronger than pronation. Also, it is wise to adopt a single standard version for most screwing valves in order to eliminate confusion under stress in the field.

Figure 2:
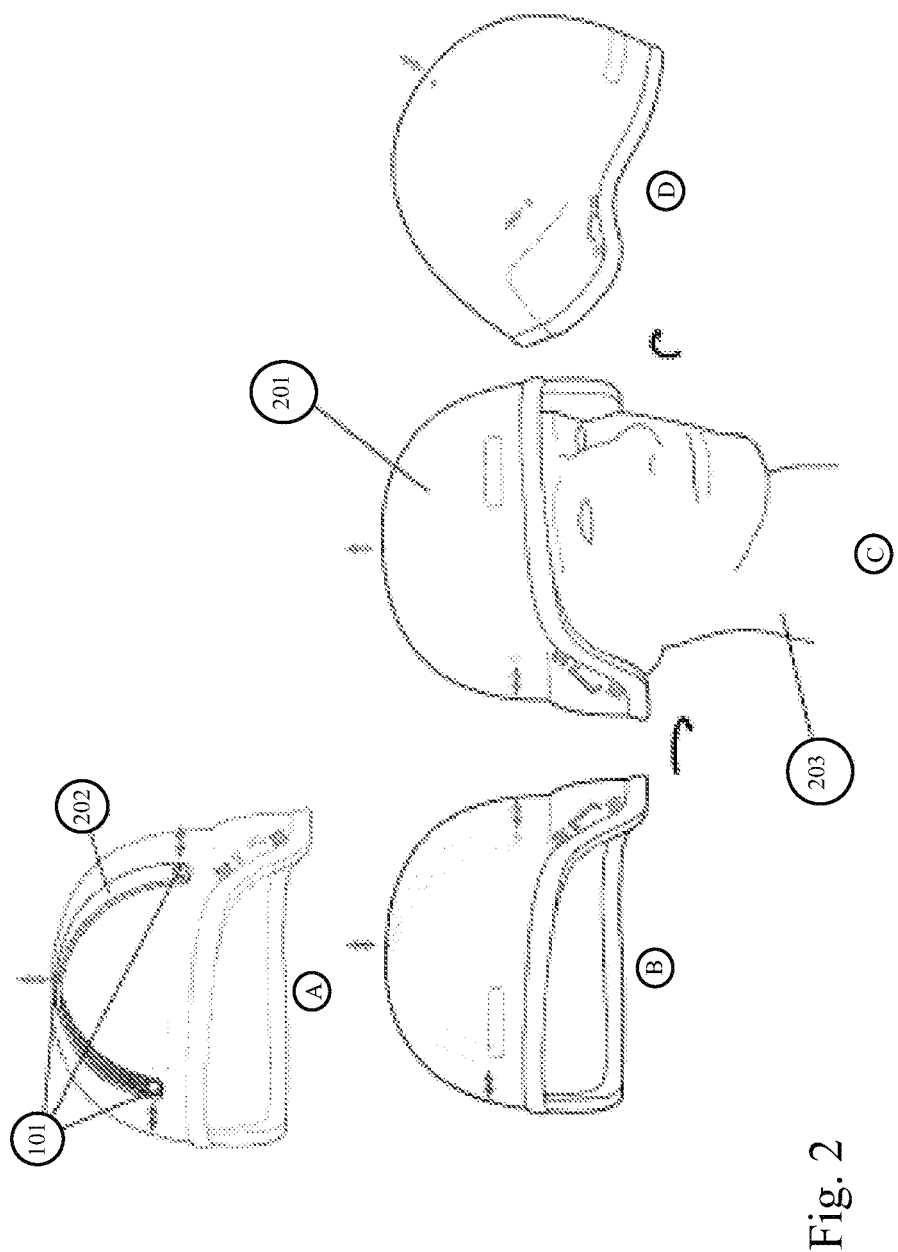
FIG. 2 A-D shows in detail the location of three bi-directional valves along an military helmet headwear of this disclosure.

FIG. 2 A-D shows in detail the location of three bi-directional valves 101 along the headwear 202 of the helmet body 201 in use by user 203. One bi-directional valve 101 (indicated by bi-directional arrows) is positioned at the top and two other bi-directional valves 101 are positioned at lateral sides.

Figure 3:
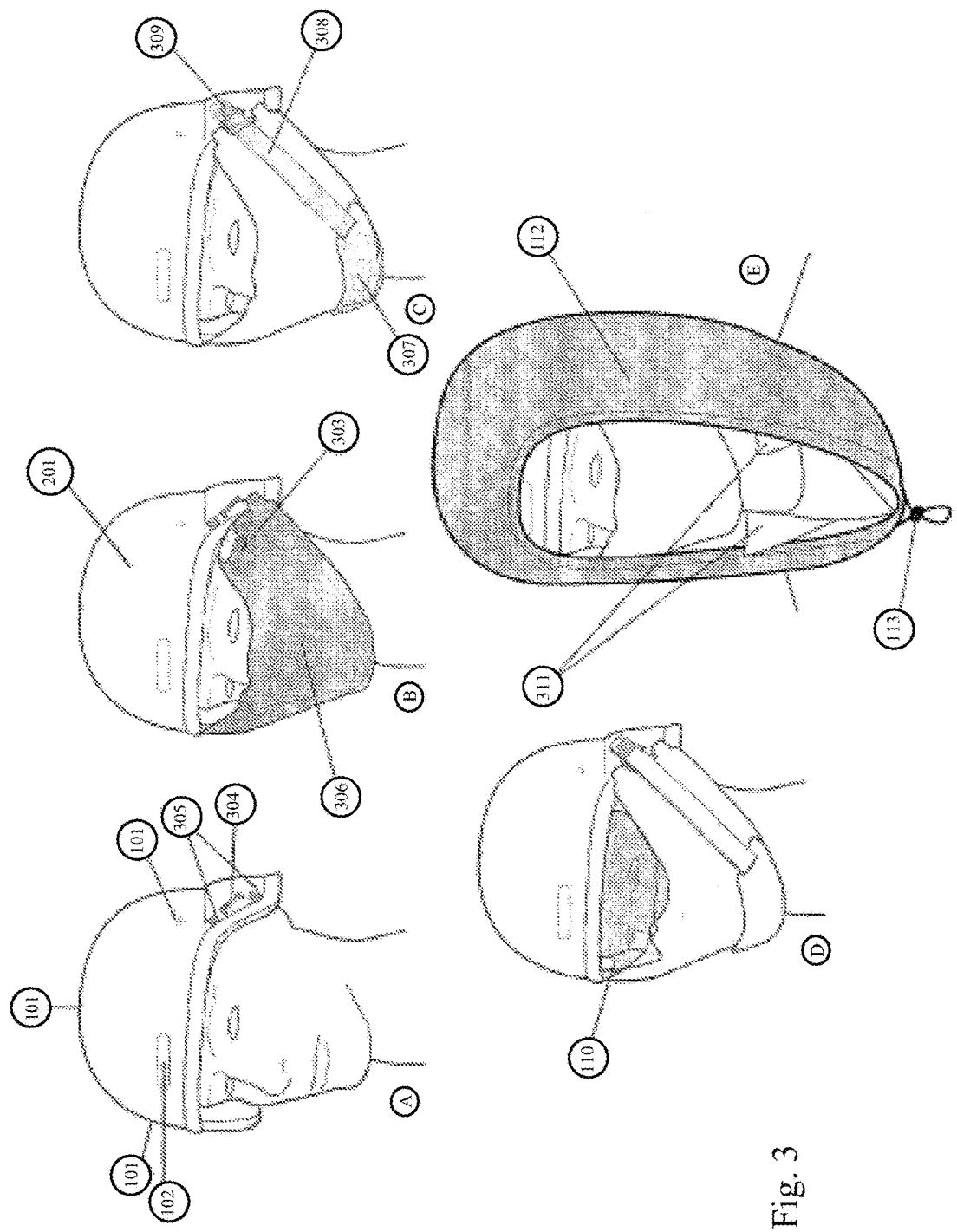
FIG. 3 A-E is a perspective view of an military helmet of this disclosure having a face-mask, visor and thermo-insulating hood attached to the helmet to create a temperature barrier.

FIG. 3 is a perspective view of the military helmet. Additional features of the military helmet include a visor 110, a face mask 306 and a thermoinsulating hood 112, which are attached to the military helmet after the cooling is implemented and positioned to insulate the head, and to prevent loss of cooling and a concomitant increase in brain temperature. The three bi-directional valves 101 are positioned along the brain cooling system, inside the helmet body 201. A color indicative gauge 102, which displays variable colors dependent upon the temperature of the brain cooling system, is also included. Velcro fasteners/straps 303 and 305 are attached to the thermoinsulating mask 306 and helmet body 201, respectively. A fix mount 304, which protrudes from the helmet body 201, is designed for rapid connection 309 with two stiff side straps 308 and stabilization of the chin-strap holder 307. A collar 311 of a user's combat jacket with snaps 704 (not shown) attached is encompassed by the thermoinsulating hood 112, which further encompasses the helmet body 201, and can be tightened, in the front, with a toggle 113.

Figure 4:
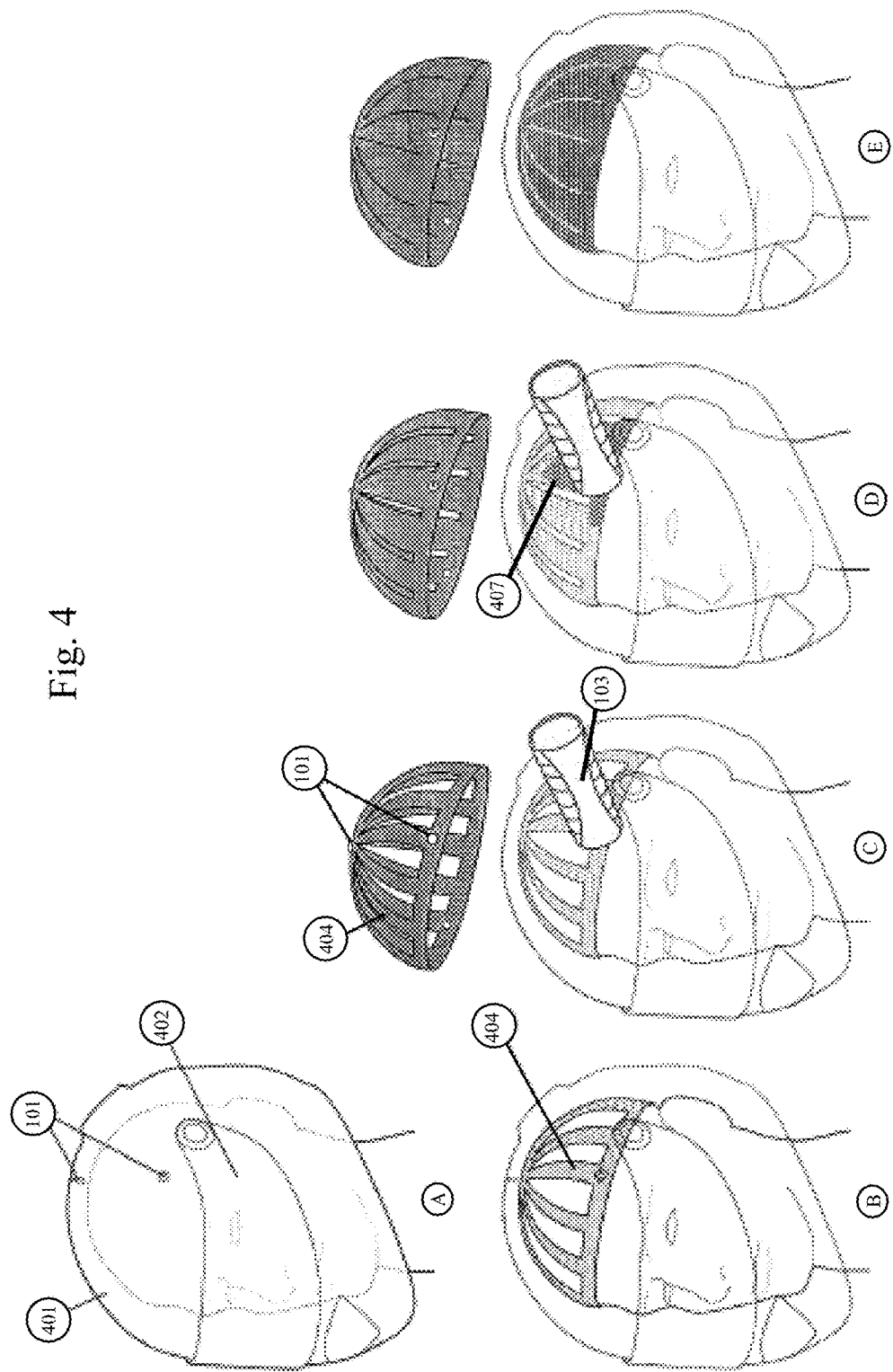
FIG. 4 A-E diagrammatically shows a non-military helmet brain cooling system of this disclosure.

FIG. 4 diagrammatically shows another form of apparatus of the disclosure comprising a non-military helmet cooling system. The non-military helmet system has a single inflatable crown pad 404 attached to a non-military helmet body 401 and connected to a plurality of bi-directional valves 101, performing like a tight head-cap when inflated, as shown in FIG. 4 B-E by coolant from the canister/can 103. The non-military helmet brain cooling system includes a non-military visor 402 at the front, which helps to insulate the head and prevent loss of cooling. The dynamics of filling the crown pad 404 is illustrated by replacing areas of light gray tones with dark shadows 407 and concomitant closure of the gaps in the body of the crown 404 as shown in FIG. 4 C-E.

Figure 5:
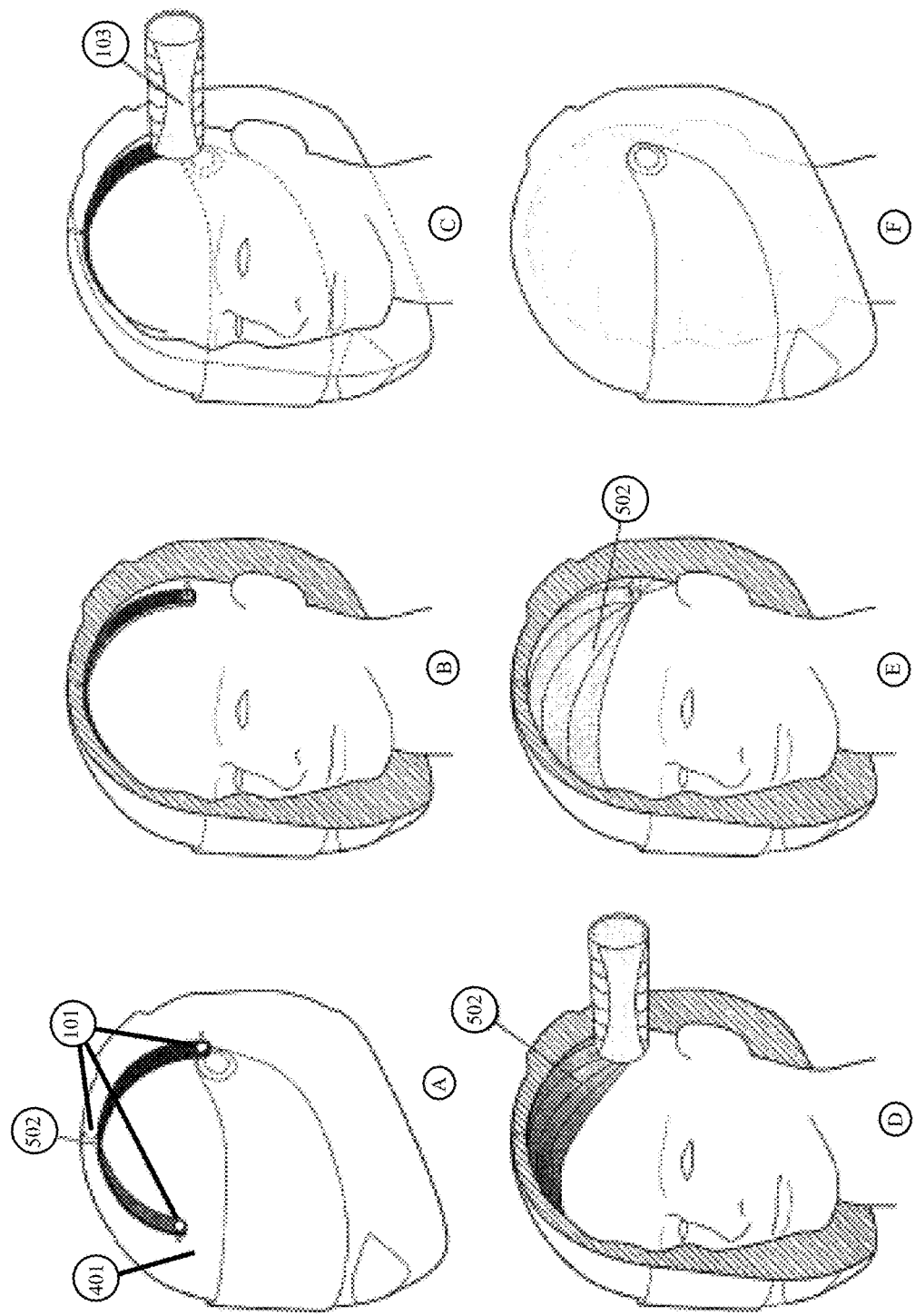
FIG. 5 A-F depicts a cross-sectional view of portions of a non-military helmet brain cooling system of this disclosure.

FIG. 5 depicts a cross-sectional view of portions of a non-military helmet cooling system. The non-military helmet has a single inflatable head-band 502, which is connected to three valves 101, and expands like an air-bag. The valves 101 are positioned at the upper middle and at each lateral side of the non-military helmet body 401. In this embodiment, the non-military helmet body 401 has a head-band 502, which is comprised of 2-8 cushioned pads, which are positioned peripherally to permit inflation of the head-band 502, delimiting the area of expansion of the fully-inflated gas-cooled pad after application of the canister 103. The bi-directional valves 101 may allow the controlled release of pressure. The three valves 101 are aligned along the head-band 502 avoiding the need to move the injured head to implement the cooling mechanism.

Figure 6:
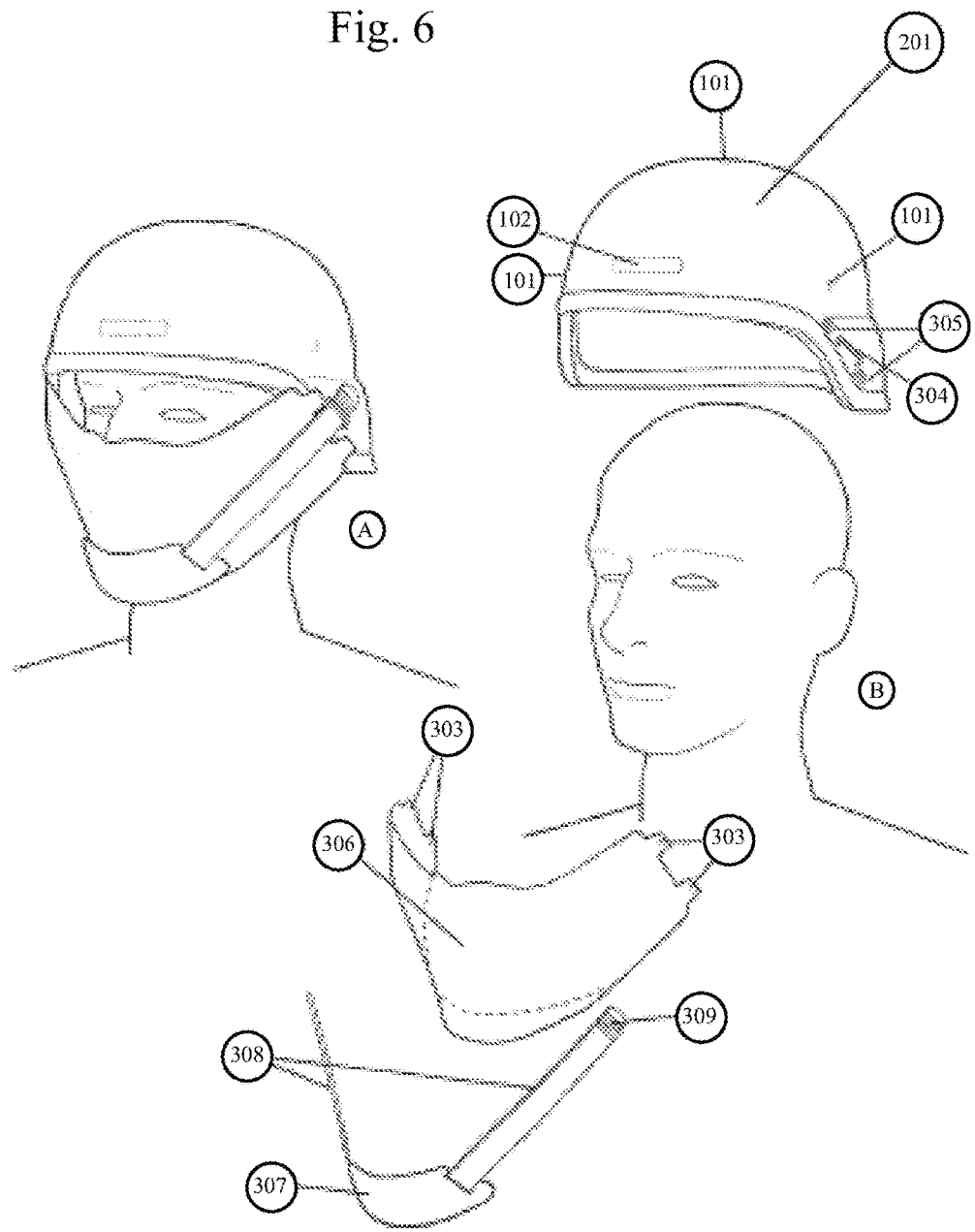
FIGS. 6 A and B is a perspective view of some of the additional features of a military helmet brain cooling system of this disclosure, e.g., bi-directional valves, a color indicative gauge, which displays temperature as variable colors, a protective face guard/mask, and a chin-strap holder.

FIG. 6 shows a perspective and exploded view of additional features of the military helmet. The military helmet has bi-directional valves 101, a color indicative gauge 102, which displays temperature as variable colors, a protective face guard/mask 306, which is thermoinsulated and engages with Velcro fasteners/straps 303, and a chin-strap holder 307, which is slidable on two stiff side straps 308. The straps 308 have easily graspable ends 309 that connect to the helmet body 201 at the fix mount 304 and can be pulled to fit the jaw, but which allow the chin-holder to move with the user's jaw.

Figure 7:
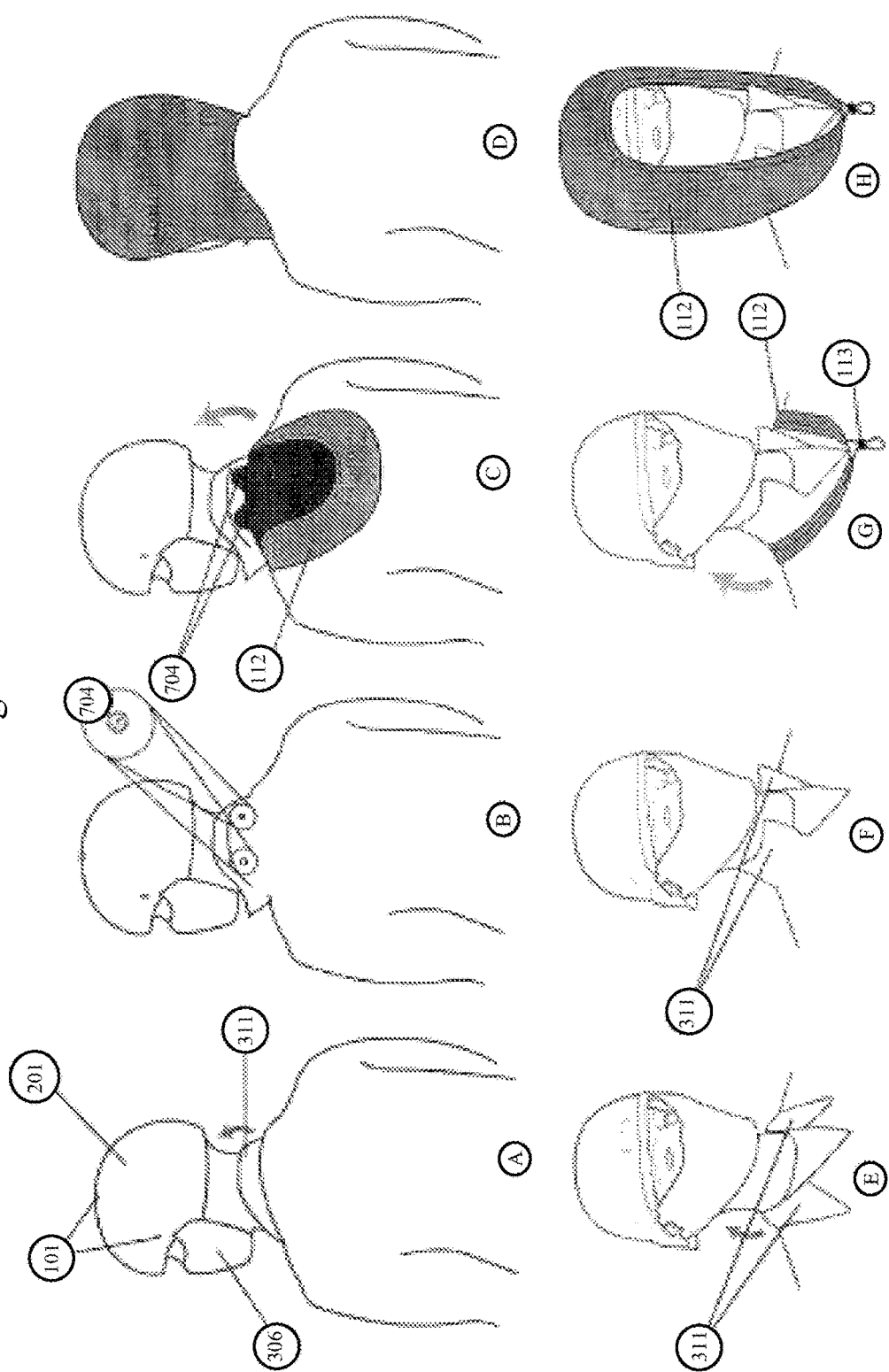
FIG. 7 A-H is a perspective view of the thermoinsulator hood for use in a military helmet brain cooling system of this disclosure.

FIG. 7 is a perspective view of the thermoinsulator hood 112 and collar 311 for use in a military helmet system by a soldier. FIG. 7 A-D shows a rear view, the thermoinsulator hood 112 is attached to snaps 704, localized at the back of the collar 311 of the soldier combat jacket with a toggle 113 at the front permitting tightening of the hood 112 to insulate the head of the injured user. Alternatively, where snaps 704 are not present on the collar 311 of the jacket, the hood 112 can be connected to a separate, attachable collar 311 placed around the neck of the injured patient. A set of snaps 704 localized at the back of the collar 311 are revealed when the collar 311 is lifted as shown in FIG. 7 E-F. The collar 311 may perform simultaneously as an inflatable cooling collar 311 and a base to attach snaps 704. The collar 311 may contain one or more bi-directional pressure-sensitive valves 101 (not shown) that are positioned for receiving a coolant filled canister. The collar may also have various structural components such as the inflatable pads or other features found throughout the rest of the present invention or accessories such as buttons, shoulder pads, collar stiffeners and zip fasteners. Additionally, FIG. 7 depicts a thermoinsulating mask 306 and bi-directional valves 101.

Figure 8:
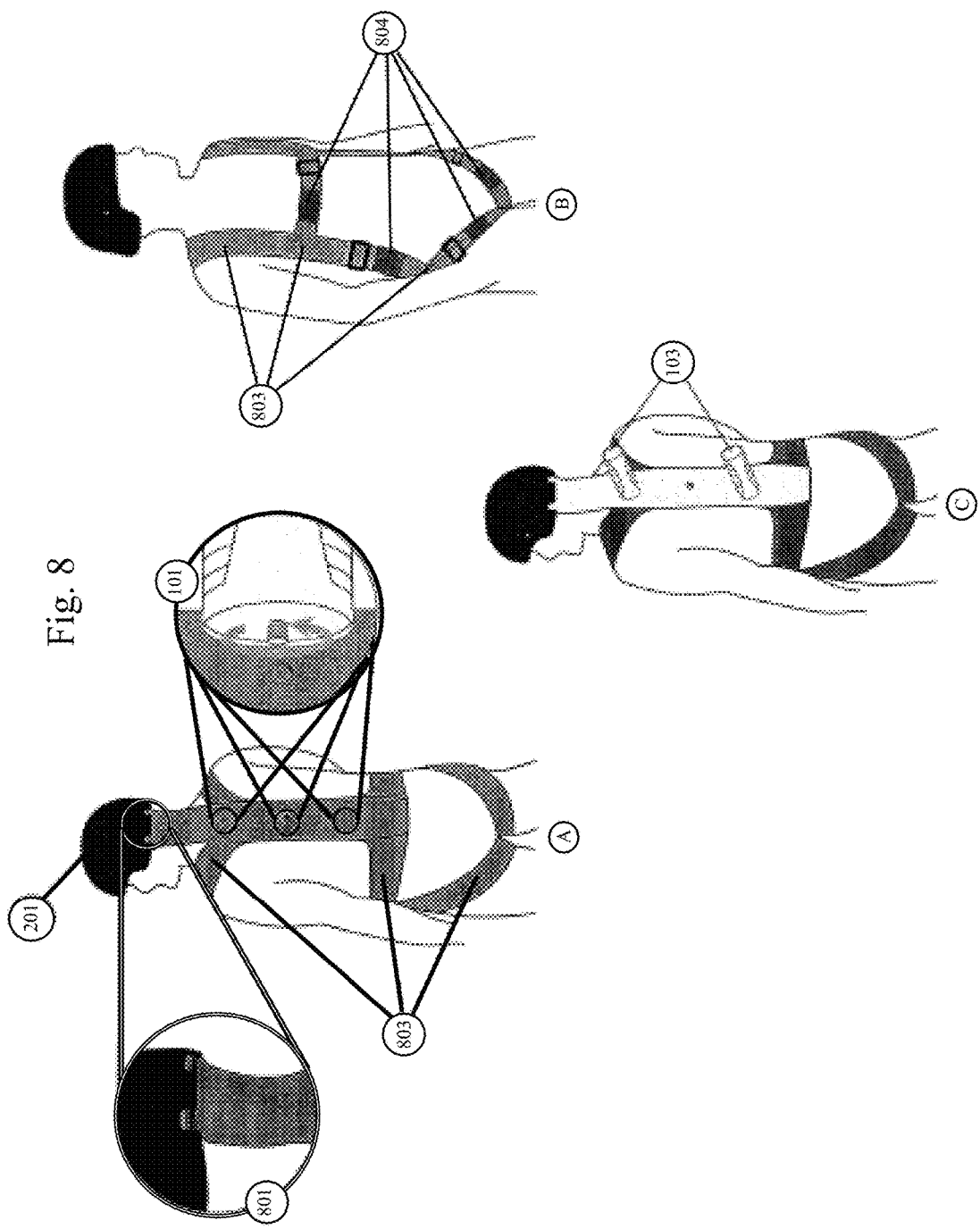
FIG. 8 A-C is a perspective view of an military helmet brain and spinal cord cooling system of this disclosure.

FIG. 8 is a perspective view of an embodiment of the spinal cord cooling system. In this embodiment, the spinal cord cooling system has a single inflatable strap 801. The strap 801 is attached to the back of the helmet body 201, which may accommodate a single expandable gas-filled cushion 106 (not shown). The inflatable strap 801 is inflated with gas released from canisters/cans 103 inserted into one of the bi-directional valves 101 positioned at the top, middle or bottom sides of the body of the strap 801, avoiding the need to move the injured neck or spinal cord to implement the cooling mechanism. The valves 101 are bi-directional, allowing the controlled release of pressure. Additional features of the spinal cord cooling system include a set of parachute-like straps 803, which are attached to the body of the patient using fasteners 804 to properly position and stabilize the hypothermic system.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. All references cited in this specification, and their references, are incorporated by reference herein in their entirety where appropriate for teachings of additional or alternative details, features, and/or technical background.

What is claimed is:

1. A helmet for protection of a user's brain, said helmet comprising:
   a. a helmet body;
   b. one or more inflatable pads attached to, but not comprising a surface of, said helmet body, wherein each of the one or more inflatable pads accommodate an expandable gas-filled balloon;
   c. one or more bi-directional pressure-sensitive valves;
   d. a temperature-sensitive probe capable of determining the user's brain temperature; and
   e. at least one coolant source capable of inflating said inflatable pads with coolant thereby cooling the user's brain; wherein the coolant is a mixture of a liquid and a gas capable of providing a cooling rate to the brain ranging from about 0.1° C. to about 0.5° C./hour.

2. The helmet of claim 1, wherein the helmet is capable of lowering the user's brain temperature to a mean temperature ranging from about 33° C. to about 36° C.

3. The helmet of claim 2, wherein the helmet is capable of maintaining the temperature of the user's brain within the range of about 33° C. to about 36° C. for about 24 hours to about 96 hours.

4. The helmet of claim 3, wherein the helmet is capable of maintaining the temperature of the user's brain within the range of about 33° C. to about 36° C. for about 48 hours to about 72 hours.

5. The helmet of claim 4, wherein the helmet is capable of maintaining the temperature of the user's brain within the range of about 33° C. to about 36° C. for about 48 hours to about 56 hours.

6. The helmet of claim 1, wherein the helmet is capable of cooling the user's brain to a mean temperature of about 33° C. to about 36° C. within about 24 hours.

7. The helmet of claim 1, wherein the helmet is capable of cooling the user's brain to the mean temperature of about 33° C. to about 36° C. within about 48 hours.

8. The helmet of claim 1, wherein the coolant is capable of providing a cooling rate to the user's brain ranging from about 0.1° C. to about 0.4° C./hour.

9. The helmet of claim 1, wherein the coolant is capable of providing a cooling rate to the user's brain ranging from about 0.1° C. to about 0.3° C./hour.

10. The helmet of claim 1, wherein the coolant is capable of providing a cooling rate to the user's brain ranging from about 0.2° C. to about 0.3° C./hour.

11. The helmet of claim 1, wherein the bi-directional pressure-sensitive valves are positioned at the top and lateral sides of the helmet body.

12. The helmet of claim 1, wherein the one or more bi-directional pressure-sensitive valves permits a varying amount of gas flow into the inflatable pads.

13. The helmet of claim 1, further comprising a face-mask attached to the helmet body to create a temperature barrier.

14. The helmet of claim 1, further comprising a visor attached to the helmet body to create a temperature barrier.

15. The helmet of claim 1, further comprising one or more inflatable spinal cord straps.

16. The helmet of claim 1, further comprising a collar adapted to enhance the induction of brain cooling by decreasing the temperature of arterial blood passing through the user's neck.

17. The helmet of claim 1, wherein the helmet provides uniform cooling to the surface area of the user's brain's frontal, parietal and occipital lobes.

18. The helmet of claim 1, wherein the helmet body is a military helmet.

19. The helmet of claim 1, wherein the helmet body is a non-military helmet.

20. A method of treating a user by adapting a helmet body to incorporate a brain cooling system comprising:
   a. attaching a plurality of inflatable interconnected pads to a helmet body so that the inflatable interconnected pads do not comprise a surface of said helmet body, wherein each of the one or more inflatable pads accommodate an expandable gas-filled balloon;
   b. incorporating one or more bi-directional pressure-sensitive valves into the helmet body;
   c. connecting said valves to the inflatable interconnected pads;
   d. connecting at least one canister containing cooling gases to said valves;
   e. inflating said inflatable interconnected pads with the cooling gases; and
   f. monitoring at least one temperature-sensitive probe to determine the user's brain temperature.

21. The method of claim 20, further comprising lowering the user's brain temperature to a mean temperature ranging from about 33° C. to about 36° C.

22. The method of claim 21, further comprising maintaining the temperature of the user's brain within the range of about 33° C. to about 36° C.

23. The method of claim 20, further comprising using a collar to enhance the induction of brain cooling by decreasing the temperature of arterial blood passing through the user's neck.

24. The method of claim 20, further comprising giving the user an anesthetic.

25. The method of claim 20, further comprising giving the user an intravenous saline solution.

* * * * *